United States Patent [19]

Bennett et al.

[11] Patent Number: 4,767,326
[45] Date of Patent: Aug. 30, 1988

[54] CARTRIDGE CONTAINER AND EJECTOR PISTON THEREFOR

[75] Inventors: Douglas D. Bennett, Cambridge, Md.; Earl C. Francis, Milford, Del.

[73] Assignee: Dentsply Research & Development Corp., Milford, Del.

[21] Appl. No.: 934,777

[22] Filed: Nov. 25, 1986

[51] Int. Cl.⁴ ............................................. A61C 5/04
[52] U.S. Cl. ........................................ 433/90; 433/89
[58] Field of Search ............... 433/90, 89, 80; 604/21, 604/38, 121, 218; 222/325, 384, 522

[56] References Cited

U.S. PATENT DOCUMENTS

| | | | |
|---|---|---|---|
| 181,226 | 8/1876 | Emde | 604/218 |
| 860,555 | 7/1907 | Middaugh | 433/90 |
| 2,505,028 | 4/1950 | Boeger | 433/90 |
| 3,462,840 | 8/1969 | Ellman | 433/90 |
| 3,618,216 | 11/1971 | Jaeger | 433/90 |
| 4,391,590 | 7/1983 | Dougherty | 433/90 |
| 4,560,352 | 12/1985 | Neumeister et al. | 433/90 |

Primary Examiner—John J. Wilson
Attorney, Agent, or Firm—Edward J. Hanson, Jr.; David E. Wheeler

[57] ABSTRACT

A miniature capsule-like cartridge adapted to be operated by being mounted in an ejector holder and including a tubular body of uniform inner diameter open at one end and the other end being closed but having a discharge opening therein, the body containing a complementary piston having an innermost pressure end complementary to the interior of the closed end of the body end and provided with an integral thin cylindrical wall at least precisely complementary in outer diameter to the inner diameter of the tubular body and extending axially away from the pressure end of the piston, the piston being operable by a piston post integral at one end with and extending axially away from the pressure end of the piston and connected to the thin cylindrical sleeve by a reinforcing rib extending integrally therebetween.

4 Claims, 1 Drawing Sheet

CARTRIDGE CONTAINER AND EJECTOR PISTON THEREFOR

BACKGROUND OF THE INVENTION

In the art of dispensing cartridges it is common practice at present, for example, to provide, in particular, the dental profession with such devices which are preloaded with cements, filling material and the like. The cartridges are mounted in ejector-type holders having operating handles or levers and, by operation thereof, desired amounts of the material in the cartridges are discharged readily and precisely.

One example of a cartridge of interest to the present invention comprises the subject matter of prior U.S. Pat. No. 4,391,590 to Dougherty, dated July 5, 1983, and assigned to the assignee of the present invention. In the patented structure, the body of the cartridge is cylindrical and of uniform inner diameter and in which a discharge piston is mounted in position in the open filling end of the cartridge to form both a closure and an ejecting piston. Cartridges of this type are miniature and, by way of example, have an outer diameter of about one quarter inch and an inner diameter of approximately one eighth inch. The piston, accordingly, has a complementary outer diameter of about one eighth inch and at present is composed of solid plastic material.

It has been found in operating a device of this type that, when the piston is of a solid nature, shrinkage occurs in the molded product and is of such nature that when operated in the tubular body, material to be discharged, when under pressure in the cartridge by operation of the ejector holder, can escape between the inner wall of the cartridge and outer wall of the piston to an undesirable extent.

In an effort to obviate this difficulty, it now has been found that when the piston of desired outer diameter relative to the inner diameter of the body is formed with a somewhat hollow section, such as a somewhat thin cylindrical skirt or sleeve extending outward from the pressure end of the piston, the shrinkage in the outer diameter is minimal and negligible.

To adapt this arrangement to the piston for the tubular body of the cartridge, it has been found necessary to include details which appear to be novel and full description of which details are set forth below and also are illustrated in the accompanying drawing.

SUMMARY OF THE INVENTION

It is among the principal objects of the invention to provide in an ejecting type cartridge formed by injection molding suitable plastic material or otherwise, a piston preferably having an outer diameter precisely no less than the inner diameter of the tubular body of the cartridge and provided for a substantial portion of the length thereof with a thin cylindrical sleeve extending axially away from the pressure end of the piston and having the aforementioned desired and preferred outer diameter, which structure is subject to no appreciable shrinkage as compared to the outer diameter of a solid piston of comparable diameter.

Another object of the invention is to provide the pressure end of the piston, which is complementary to the contour of the interior of the discharge end of the body of the cartridge with a thickness greater than that of the thin cylindrical sleeve to reinforce the mounting and support of a piston post encircled by said sleeve and extending axially from the pressure end of the piston a distance slightly beyond the outer end of the thin sleeve.

Details of the foregoing and of the invention and other objects thereof are set forth in the following specification and are illustrated in the attached drawings comprising a part thereof.

DETAILED DESCRIPTION OF THE PREFERRED EMBODIMENTS OF THE INVENTION

Figure 1:
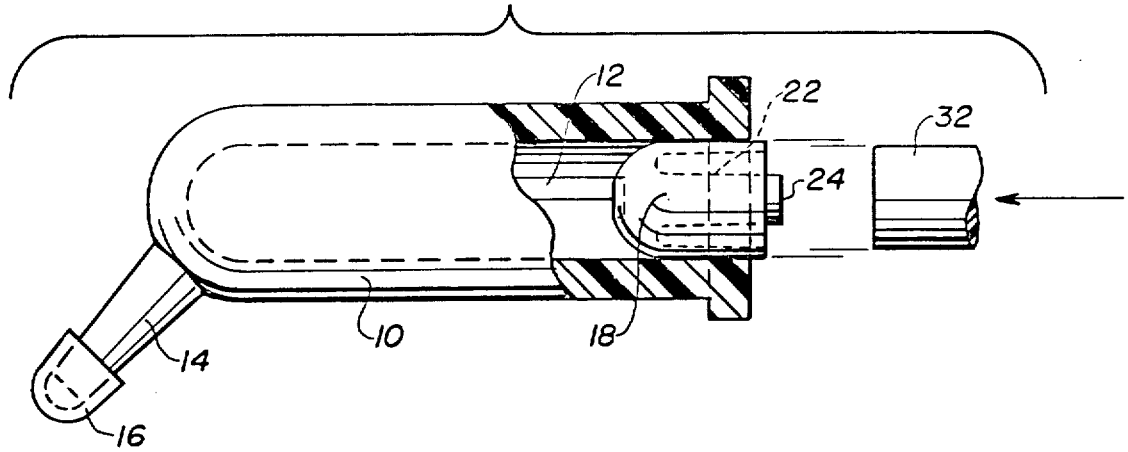
FIG. 1 is a side elevation of an explementary capsule-like cartridge to which the present invention pertains, the body of the cartridge being partly broken away to disclose a piston operable within the body, said view also showing in spaced relation to the piston, a fragmentary portion of a plunger of the type normally used to affect operation of the piston in the body of the cartridge.

Referring to FIG. 1, there is illustrated therein in suitable scale a capsule-like cartridge similar to that comprising the subject matter of prior U.S. Pat. No. 4,391,590, to Dougherty, dated July 5, 1983. The cartridge comprises a tubular body 10 which is elongated and the interior bore thereof is of uniform diameter from the outermost open end thereof to the opposite closed end. The closed end also includes and communicates with a discharge nozzle 14 over which a cap 16 is shown in closed position thereon. Preferably, the body 10 is molded from suitable plastic material for the purpose of containing various types of material useful in dentistry and otherwise, such as cements, filling material, and other similar, usually viscous type materials which require extrusion in desired small quantities.

In the structure of the prior patent referred to herein above, a solid piston molded from suitable plastic material was utilized to effect discharge of material from the interior of the body of the cartridge. It was found that when the piston was molded in solid configuration, it experienced shrinkage after molding and this sometimes resulted in the escape of material between the inner wall of the cartridge and the outer wall of the piston and the purpose of the present invention is to correct this difficulty.

Figure 2:
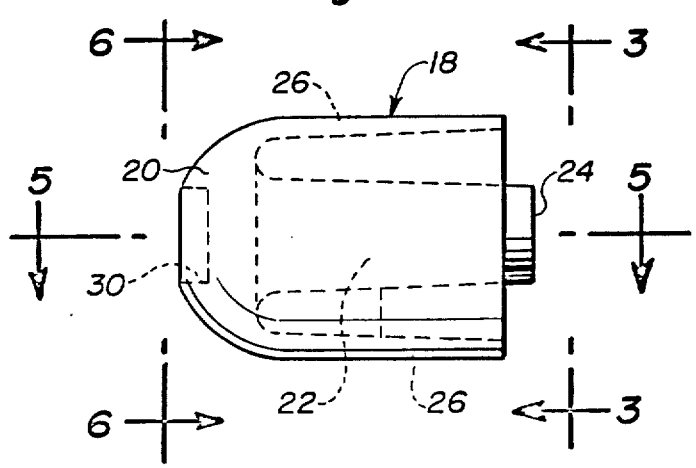
FIG. 2 is an enlarged side elevation of the piston shown in FIG. 1.
Figure 3:
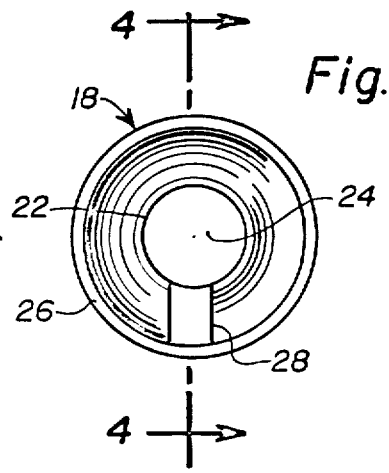
FIG. 3 is an end view of the piston shown in FIG. 2 as seen from the right hand end thereof.
Figure 4:
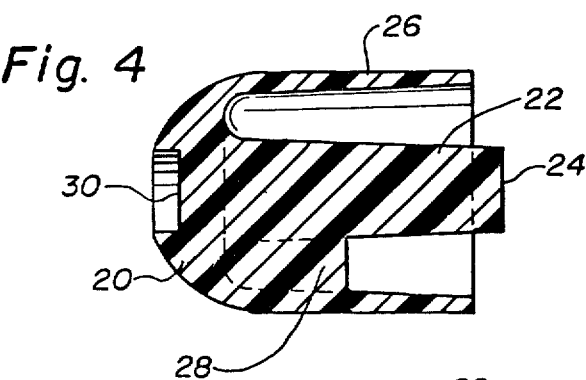
FIG. 4 is a longitudinal sectional view taken on the line 4—4 of FIG. 3.
Figure 5:
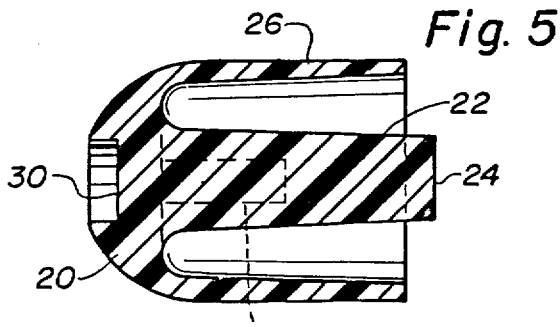
FIG. 5 is a longitudinal sectional view of the piston shown in FIG. 2 as seen on the line 5—5 thereof.
Figure 6:
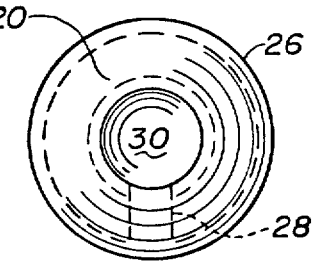
FIG. 6 is a front end view of the piston shown in FIG. 2 as seen from the left hand end thereof.

To obviate the above-described situation, piston 18 of the present invention is formed with a so called pressure end 20 which, preferably, is complementary to the inner surface of the closed end of the body 10 of the cartridge. The present invention is not to be restricted to such a limitation however. As seen particularly from FIG. 2 however in which the inner configuration of the piston is shown in dotted lines, it will be seen that the nose or pressure end of the piston 18 is relatively thick in an axial direction for a specific purpose. Molded integrally with said nose and perpendicular thereto is a piston post 22, the outer end 24 of which projects a short distance beyond and outwardly from the terminal end of the cylindrical thin wall 26 of the piston. Further to stabilize the central position of the piston post 22 within the cylindrical relatively thin wall 26, the present invention provides a radially extending intergral rib 28 between the inner surface of the thin wall 26 and one side of the piston post 22.

The foremost surface of the pressure end 20 of the piston is formed with a small cylindrical cavity 30 which primarily is of concern in conjunction with the molding of the piston and has no function in the present invention but is illustrated for the purpose of completeness.

From the foregoing description, it will be seen that in view of the relativity thick pressure end 20 of the piston, and the fact that the piston post 22 is integral therewith and connected thereto at the forward end of the piston, when pressure means such as a plunger 32 which is fragmentarily illustrated in FIG. 1, engages the piston, it will contact only the terminal outer end 24 of the post 22 and not the rim of the relatively thin sidewall 26. By such arrangement, no damage will be incurred by the sidewall 26 when the piston is engaged by the plunger 32. From FIG. 1 however, it will be seen that preferably the diameter of the plunger 32 is slightly less than the outer diameter of the piston 18 and particularly the diameter of the thin sidewall 26 thereof.

In operation, therefore, in effect, the piston somewhat resembles an umbrella and when going forward in the bore 12 of the cartridge, the nose 20 leads the way and the thin cylindrical wall 26 follows somewhat in the nature of a sleeve which extends rearwardly from the thickened forward end 20 of the piston. Under such circumstances, it is possible and preferable to mold the piston 18 with an outer diameter substantially uniform and definitely no less than equal to the inner diameter of the interior bore 12 of the cartridge body 10. Due to the thinness of the wall 26, it is therefore found that when the outer dimeter of the wall 26 is at least equal to and no less than the inner diameter of the interior bore 12 of the body 10 of the cartridge, there is a very close wiping and seal effect between the piston wall 26 and bore 12 and substantially no tendency for material to escape between the outer surface of the wall 26 of the piston and inner surface 12 of tubular body 10 and even when the outer diameter of the thin cylindrical wall 26 is of slightly greater diameter, such as of the order of several thousandths of an inch, than the inner diameter of the interior bore 12 of the body 10 of the cartridge, a firm wiping effect still exists between the wall 26 and the interior bore 12 of the cartridge, without deformation of the piston wall.

Further to understand and appreciate the significance of the foregoing, it is appropriate to indicate that the present invention pertains to relatively miniature items. For example, and without restriction thereto, the outer diameter of the tubular body 10 preferably is approximately 0.258" and the inner diameter of bore 12 is approximately 0.160". Accordingly, the outer diameter of piston 18 preferably is 0.160" or no less than that dimension and may be several thousandths in excess of it. Further, the thickness of the cylindrical thin wall 26 at the outer rim thereof, is approximately 0.010" to 0.020", so it can be appreciated that the wall is quite thin and therefore has desireable but limited flexibility to adhere faithfully to the cylindrical inner wall surface of the interior bore 12 of the tubular body 10. From FIG. 2, also, it can be seen that the length of the actual thin cylindrical wall 26 of the piston 18 extends from the thicker nose end thereof for at least three fourths of the overall length of the entire piston and, inoperation, due to the provision of the radial rib 28, the piston post 22 is afforded ample stability centrally of the piston.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

We claim:

1. A cartridge adapted to be operated by being mounted upon an ejector-type holder and comprising in combination, a hollow cartridge body having an elongated uniformly cylindrical inner wall of constant diameter and open at one end to receive a piston, the opposite end of said body being closed by an end integral therewith and having a discharge opening therein, and a piston having an operative pressure end nearest the closed end of the said body, said piston also having a thin cylindrical sleeve extending integrally with and axially from said pressure end of said piston and said cylindrical sleeve having an outer diameter no less than the diameter of said cylindrical inner wall of said body and adapted to closely and slidably engage the inner wall of said body when said piston is moved inwardly toward the closed end of said body, and a piston post positioned co-axially within said thin cylindrical sleeve of said piston and integral at one end with the pressure end of said piston and adapted to be engaged by an operating pressure rod of said ejector-type holder wherein all members of said piston are injection molded from plastic material of limited flexibility and said piston post is substantially less in diameter than the inner diameter of said thin cylindrical sleeve of said piston and said piston post having stiffening means extending integrally between said post and the interior of said thin cylindrical sleeve of said piston and said stiffening means comprises an integral rib extending radially between said piston post and inner surface of said cylindrical sleeve of said piston.

2. The cartridge according to claim 1 in which said pressure end of said piston is thicker in an axial direction than the thickness of the wall of said cylindrical sleeve thereof and the inner end of said piston post is integrally connected to said pressure end of the piston centrally thereof.

3. A cartridge adapted to be operated by being mounted upon an ejector-type holder and comprising in combination, a hollow cartridge body having an elongated uniformly cylindrical inner wall of constant diameter and open at one end to receive a piston, the opposite end of said body being closed by an end integral therewith and having a discharge opeing therein, and a piston having an operative pressure end nearest the closed end of the said body, said piston also having a thin cylindrical sleeve extending integrally with and axially from said pressure end of said piston and said cylindrical sleeve having an outer diameter precisely no less than the diameter of said cylindrical inner wall of said body and adapted to closely and slidably engage the inner wall of said body when said piston is moved inwardly toward the closed end of said body to prevent escape of material between the wall of said body and the piston, and a piston post positioned co-axially within said thin cylindrical sleeve of said piston and integral at one end with the pressure end of said piston and adapted to be engaged by an operating pressure rod of said ejector-type holder, wherein said piston post is substantially less in diameter than the inner diameter of said thin cylindrical sleeve of said piston and said piston post having stiffening means extending integrally between said post and the interior of said thin cylindrical sleeve of said piston, and wherein the outer end of said piston post extends axially beyond the outer end of the cylindrical sleeve of the piston a limited distance to prevent engagement of said outer end of said sleeve by the end of an ejector rod or the like of an ejector-type holder when operating in discharge manner upon the cartridge.

4. The cartridge according to claim 3 in which said pressure end of said piston is thicker in an axial direction than the thickness of the wall of said cylindrical sleeve thereof and the inner end of said piston post is integrally connected to said pressure end of the piston centrally thereof.

* * * * *